US009897572B2

(12) United States Patent
Cooke et al.

(10) Patent No.: US 9,897,572 B2
(45) Date of Patent: Feb. 20, 2018

(54) DEVICES AND METHODS FOR HIGH-THROUGHPUT ASSAY (71) Applicants: Marcus S. Cooke, Miami, FL (US); Shekhar Bhansali, Weston, FL (US); Mahsa Karbaschi, Matthews, NC (US); Pratikkumar Shah, Miami, FL (US)

(72) Inventors: Marcus S. Cooke, Miami, FL (US); Shekhar Bhansali, Weston, FL (US); Mahsa Karbaschi, Matthews, NC (US); Pratikkumar Shah, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/367,988

(22) Filed: Dec. 2, 2016

(65) Prior Publication Data
US 2017/0160231 A1   Jun. 8, 2017

Related U.S. Application Data (60) Provisional application No. 62/262,734, filed on Dec. 3, 2015.

(51) Int. Cl.
*G01N 27/447* (2006.01)
*G01N 27/453* (2006.01)
*C12N 15/10* (2006.01)

(52) U.S. Cl.
CPC ..... *G01N 27/44782* (2013.01); *C12N 15/101* (2013.01); *G01N 27/44708* (2013.01); *G01N 27/44756* (2013.01); *G01N 27/453* (2013.01)

(58) Field of Classification Search
CPC .......... G01N 27/447; G01N 27/44791; G01N 27/44734; G01N 27/453; G01N 27/44756; C12N 15/01; C12N 15/101
See application file for complete search history.

(56) References Cited

U.S. PATENT DOCUMENTS

| 5,963,456 A * | 10/1999 | Klein ............... G01N 27/44721 204/451 |
| 8,062,592 B2 * | 11/2011 | Ozawa ............. G01N 27/44708 204/604 |

FOREIGN PATENT DOCUMENTS

WO   WO 2015/025123 A1   2/2015

OTHER PUBLICATIONS

"Instruction Manual for the COMPAC-50 High Throughput Comet Electrophoresis System", Cleaver Scientific Ltd. believed published sometime in 2014.*

(Continued)

*Primary Examiner* — Alexander S Noguerola
(74) *Attorney, Agent, or Firm* — Saliwanchik, Lloyd & Eisenschenk (57) ABSTRACT

Apparatuses and associated methods for manipulating an assembly of glass slides employed in cellular assay processes are provided. Each apparatus can accommodate at least one removable rack of slides to undergo electrophoresis in a comet assay. The slides can remain in the same apparatus while being subjected to a sequence of fluid staining and washing with temperature control, advantageously shortening the amount of time required for processing the slides by keeping them in the same work station for the entire duration of the assay.

7 Claims, 6 Drawing Sheets (56) References Cited

OTHER PUBLICATIONS

Laboratory news article on the COMPAC-50 Comet Assay Tank published by LabBulletin, Oct. 8, 2014.*

Product literature for the CS-300V Power Supply, Cleaver Scientific Ltd., publication date unkown.*

COMPAC-50 HTP Comet Assay Tank, $1^{st}$ ed. Warwickshire, p. 1; www.cleaverscientific.com.

Karbaschi, M., Cooke, M.S., "Novel method for the high-throughput processing of slides for the comet assay." *Sci. Rep.*, Nov. 2014, 4: 7200, doi:10.1038/srep07200.

Shaposhnikov, S. et at., "Increasing the resolution of the comet assay using fluorescent in situ hybidication—a review." *Mutagenesis*, Jun. 2009, 24(5): 383-389, doi:10.1093/mutage/gep021.

Sathya, T. et al., "Genotoxicity evaluation of certain Bhasmas using Micronucleus and Comet assays." *The Internet Journal of Alternative Medicine*, 2009, 7(1): 1-6.

* cited by examiner

DEVICES AND METHODS FOR HIGH-THROUGHPUT ASSAY

CROSS-REFERENCE TO A RELATED APPLICATION

This application claims the benefit of U.S. provisional application Ser. No. 62/262,734, filed Dec. 3, 2015, which is incorporated herein by reference in its entirety.

BACKGROUND OF INVENTION

Single-cell gel electrophoresis, also known as a "comet assay", is a process by which DNA damage is quantified in individual cells. The process may be run under neutral conditions where strand breaks in DNA are identified or under alkaline conditions where alkali-labile sites or certain nucleobase modifications are identified. The principle of single-cell gel electrophoresis is that strand breaks lead to relaxation and unwinding of DNA under alkaline conditions. By subsequently applying an electric field, the DNA undergoes electrophoresis, moving under the influence of the electric field and forming a "comet" shape when viewed under a microscope. The amount of DNA in the comet "tail" relative to the amount remaining in the comet "head" is proportional to the number of strand breaks present. This ratio provides a quantified measure of the DNA damage present in a cell of interest.

Damage that can be detected by a comet assay include, for example, alkali labile sites, oxidatively generated nucleobase damage, double strand breaks, single strand breaks, and DNA cross-linking with other DNA or protein. The comet assay can also be used to measure DNA repair by noting the smaller size of the comet tail compared to damaged DNA after a given amount of time.

Figure 1:
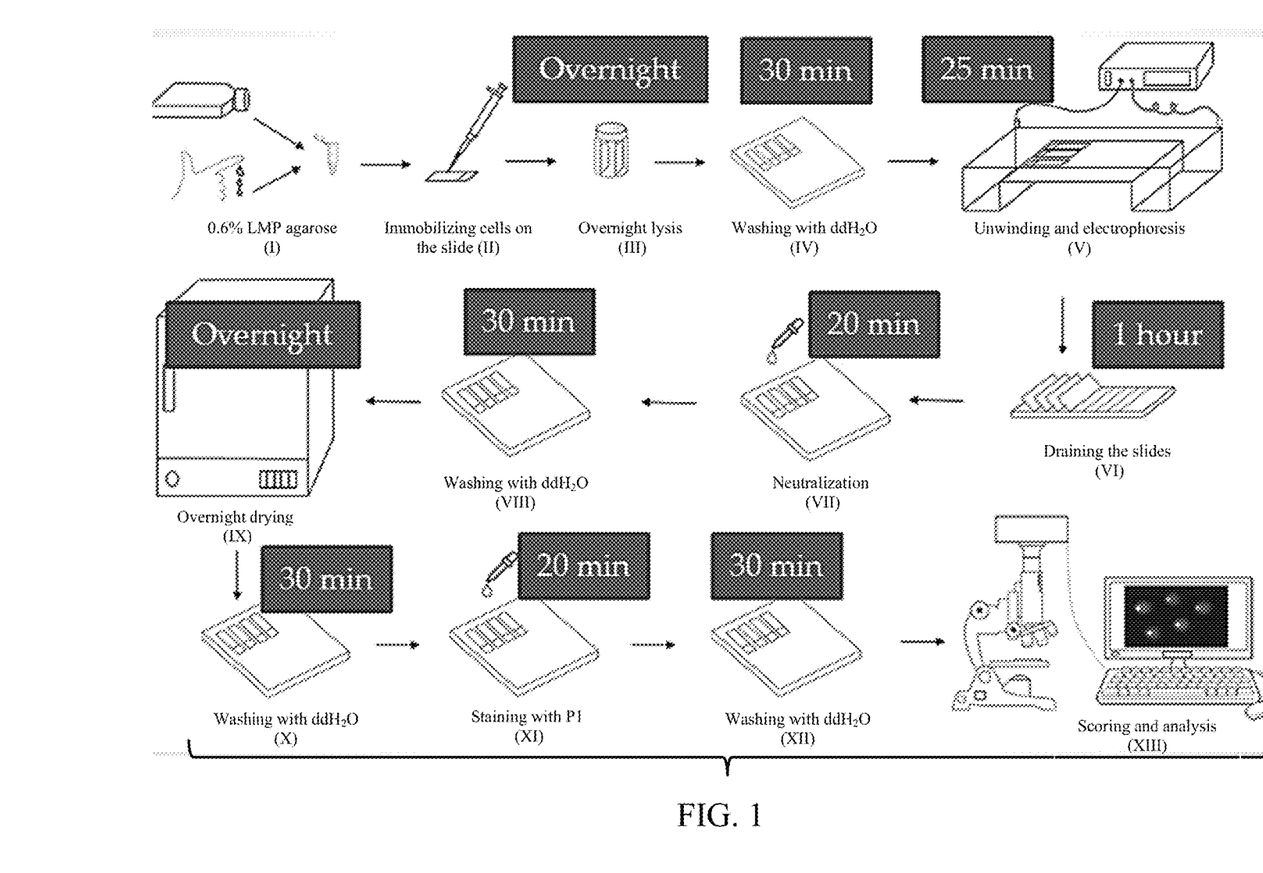
FIG. 1 shows an overview of conventional alkaline-based comet assay procedures.

Single-cell gel electrophoresis is generally conducted in a series of steps (FIG. 1). A single cell of interest is first mixed with, and embedded in, agarose with a low melting point and then loaded onto a microscope slide, which has been pre-coated with an agarose gel matrix. After the gel matrix is allowed to set, it is then subjected to a number of pre-electrophoresis steps including lysing the cell at a high pH, washing, and optionally treating the cell with DNA repair enzymes, if needed. The presence of DNA strand breaks, and under high pH of the electrophoresis buffer, allows the cellular DNA to unwind. The slide is then transferred into an electrophoresis tank and electrophoresed. Then, a number of post-electrophoresis steps are performed including, for example, draining, neutralization, washing, staining, and drying. Finally, the cells are subjected to imaging and/or scoring for further analysis.

Although the comet assay is gaining popularity as industry and academic institutions began to adopt it for single-cell analysis and genotoxicology testing, some factors still limit its implementation. These factors include, for example, low sample throughput, inaccurate temperature control, and long sample workup procedure. Additionally, the numerous pre- and post-electrophoresis steps complicate the manipulation of multiple slides. In currently available methods, slides must be handled individually through each step, making the process laborious and time-consuming. Moreover, lengthy manipulation of slides presents an increased risk that the gels may become damaged, contaminated, or lost.

Methods presented previously in publications such as, for example, WO 2015025123, have improved comet assay efficiency by increasing the number of slides that can be accommodated during the assay process. However, there still remains a need of streamlining the assay such that the extent of slide manipulation can be reduced and the potential for automating the process can be improved.

In the past, the focus on increasing the rate of processing throughput had been placed on automating the scoring process, as it has been considered a bottleneck to the overall processing efficiency. However, with the automated scoring being improved recently, attention has been focused on streamlining other aspects of the comet assay to improve its throughput, particularly in slide manipulation and process automation.

BRIEF SUMMARY

The subject invention provides apparatuses and associated methods for manipulating an assembly of glass slides employed in cellular assay processes.

Exemplary embodiments provide an apparatus for accommodating at least one removable rack of slides to undergo electrophoresis in a comet assay. In preferred embodiments, the at least one rack of slides can remain in the same apparatus while being subjected to a sequence of fluid staining and washing with temperature control, advantageously shortening the amount of time required for processing the slides by keeping them in the same work station for the entire duration of the assay.

In more preferred embodiments, the control of fluid and temperature within the apparatus is automated.

In specific embodiments, electrical field can be applied directly to the apparatus during an electrophoresis process.

Advantageously, the subject invention provides technology for streamlining the entire process of a cellular assay (e.g., the comet assay) prior to scoring, allowing for consistent and accurate temperature control as well as preventing possible light contamination due to handling and transporting the slides during the assay.

Embodiments of the apparatus of the subject invention provide a more reliable outcome in assay experiments, while allowing lab technicians work more efficiently by relinquishing the need of constant supervision during the assay process, while providing more reliable assay results. Advantageously, the automated apparatus can be compact, a much sought-after feature that allows the apparatus to take up less bench space in laboratories.

DETAILED DISCLOSURE

The subject invention provides apparatuses and associated methods for manipulating an assembly of glass slides employed in cellular assay processes.

Exemplary embodiments provide an apparatus for accommodating at least one rack of slides to undergo electrophoresis in a comet assay. In preferred embodiments, the at least one rack of slides can remain in the same apparatus while being subjected to a sequence of fluid staining and washing with temperature control, advantageously shortening the amount of time required for processing the slides by keeping them in the same work station for the entire duration of the assay.

In more preferred embodiments, the control of fluid and temperature within the apparatus is automated.

In specific embodiments, electrical field can be applied directly to the apparatus during an electrophoresis process.

Figure 2A:
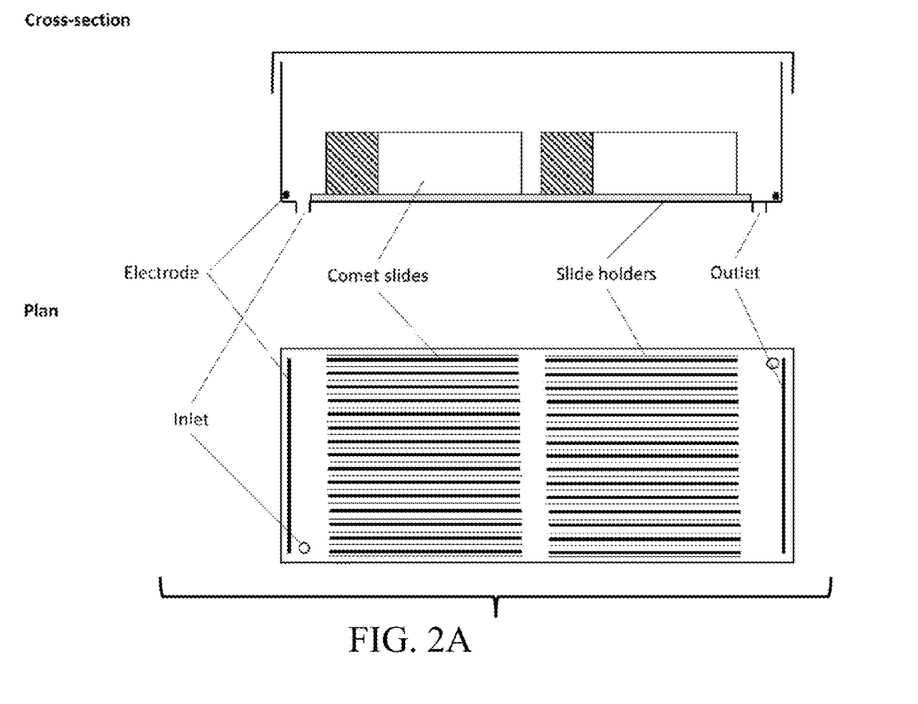
FIG. 2A shows a schematic of the cross-section, through its length, and the plan view of an embodiment of the electrophoresis tank.
Figure 2B:
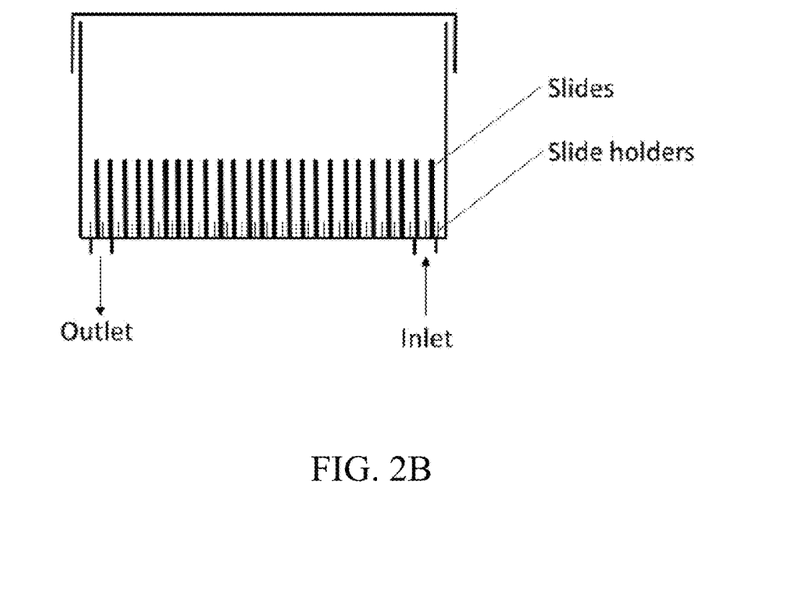
FIG. 2B shows a schematic of the cross-section, through its width, of an embodiment of the electrophoresis tank.
Figure 5:
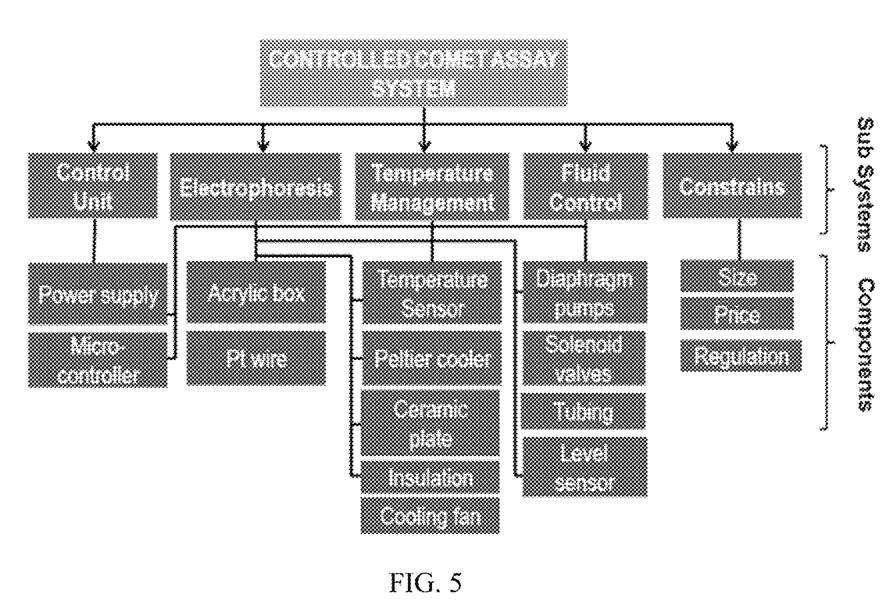
FIG. 5 shows the components of an embodiment of the comet assay apparatus.

Advantageously, the subject invention provides technology for streamlining the entire process of a cellular assay (e.g., comet assay) prior to scoring, allowing for consistent and accurate temperature control as well as preventing possible light contamination due to handling and transporting the slides during the assay. An exemplary embodiment of an electrophoresis tank of the apparatus is shown in different views in FIGS. 2A and 2B. Further, images of a preferred embodiment of the apparatus are shown in various views in FIGS. 3A, 3B, and 3C. FIG. 5 summarizes the various components of an exemplary comet assay apparatus.

In one aspect, the subject invention provides an apparatus for performing a cellular assay, preferably a comet assay, with improved processing throughput and reduced contamination during the assay process.

Figure 3A:
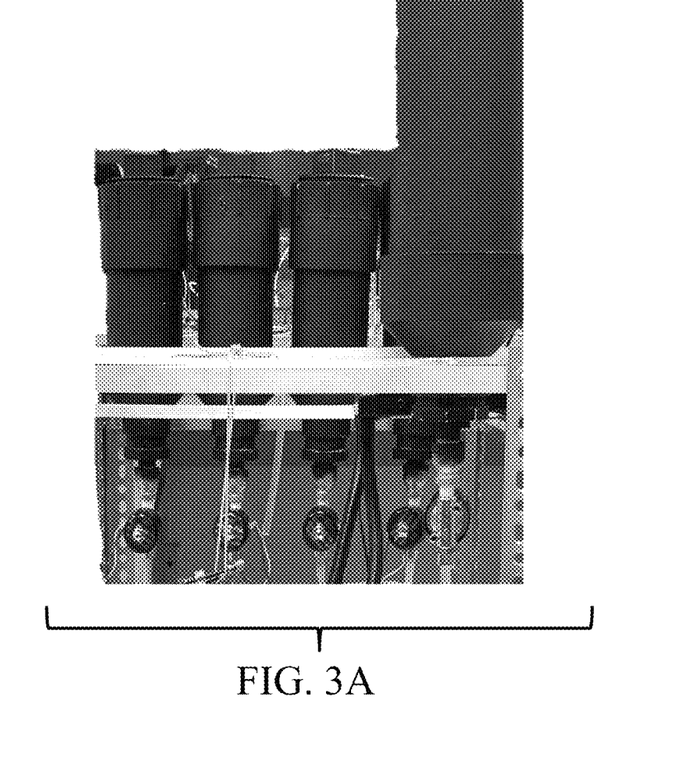
FIG. 3A shows an image of the first (i.e., top) compartment of an embodiment of the comet assay apparatus.

In some embodiments, the apparatus comprises four compartments arranged vertically, which advantageously reduces the bench space needed to complete the assay process. The top compartment comprises a water tank and at least one tank filled with a solution needed for the assay process. Each tank is equipped with its own solenoid valve for automated dispensing of the solution contained therein (FIG. 3A). In an exemplary embodiment in which a comet assay is carried out in the apparatus, the top compartment comprises one water tank and four solution tanks with each tank filled with a different solution independently selected from a lysis buffer, a neutralization buffer, an electrophoresis buffer, and a staining solution. Those skilled in the art would recognize other solutions and/or buffers may also be stored in one or more of the tanks for different assay applications.

Figure 3B:
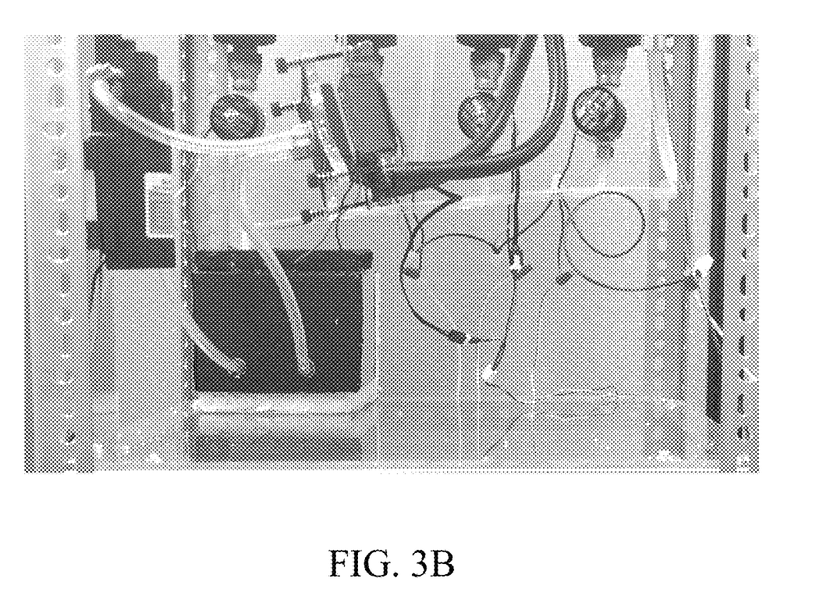
FIG. 3B shows an image of the second compartment of an embodiment of an exemplary comet assay apparatus.

In some embodiments, the compartment immediately below the top compartment comprises an insulated chiller and a cooling loop that connects together a pump, a liquid-based cooler, a thermoelectric device (FIG. 3B). In an exemplary embodiment, the liquid-based cooler is similar to one used for cooling the central processing unit of a computer. In another exemplary embodiment, the thermoelectric device is a Peltier device equipped with both cooling and heating elements. In some embodiments, the chiller is equipped with two float sensors and a temperature sensor capable of implementing temperature control of the chiller.

In some embodiments, a third compartment below the chiller comprises an electrophoresis tank and a cooling loop that circulates chilled water around the electrophoresis tank. In some embodiments, the tank comprises at least one removable rack for holding multiple individual substrates on which samples are fixated. In preferred embodiments, the tank comprises two or more removable racks. In exemplary embodiments, the individual substrates are glass slides.

In some embodiments, the electrophoresis tank comprises two electrodes located at opposite ends of the tank that are adapted to induce an electric current when connected to a power supply. Together with the fluid-dispensing and temperature-control systems, the electrophoresis tank facilitates the assay process without the need to transfer the removable racks to different work stations during the assay process. Minimizing the need to transport the slides has been reported to be important for reducing variability in the overall assay results.

Advantageously, the electrophoresis tank provided herein is designed to accommodate various rinsing, staining, neutralizing, and drying processes required by a cellular assay in a temperature- and solution-controlled environment.

In exemplary embodiments, each removable slide rack holds up to, for example, 25 glass slides. With respect to the surfaces of the slides on which cells are fixated, the slides are arranged substantially parallel to one other and non-parallel a bottom surface of the electrophoresis tank. In a particular embodiment, the glass slides are arranged perpendicular to the bottom surface of the tank. Advantageously, removable racks provided herein can each accommodate multiple slides at once, significantly increasing the efficiency of slide manipulation during assay process.

Figure 3C:
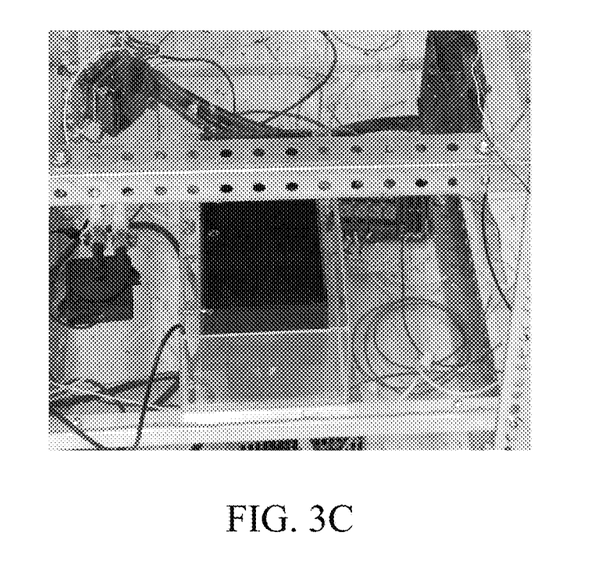
FIG. 3C shows an image of the third compartment of an embodiment of the comet assay apparatus.

In some embodiments, the subject invention provides an electronic command center for controlling the automation of the cellular assay process conducted within the apparatus. The command center, as shown in FIG. 3C, is located on the bottom compartment of the apparatus, comprising a power supply and at least one microcontroller such as, for example, an Arduino MEGA. In certain embodiments, additional electronic components of the apparatus are housed in the same compartment with the microcontroller. In some embodiments, the four compartments are interconnected with tubing (e.g., for dispensing and circulating solutions) and electrical wirings to enable the operation of the apparatus. In an exemplary embodiment, the apparatus is interfaced with an AC power supply, which can be switched on and off as well as adjusted for voltage and amperage, if necessary, with a single control.

Advantageously, components housed in the apparatus can be adapted for other cellular assays requiring precise temperature and fluid control.

In another aspect, the subject invention provides a method of performing a cellular assay, preferably the comet assay, using the apparatus provided herein. In a specific embodiment, rather than moving the at least one slide-containing rack from one staining dish to another, the racks remain in one work station (e.g., the electrophoresis tank) into which buffers and reagent are added and then drained after a period of time in accordance with the requirement of the assay process. Advantageously, this design allows a user to leave the apparatus unattended without suspending the assay process.

In certain embodiments, the assay process begins when the solenoid-controlled valves under the solution tanks open and solutions flow into the chiller that is located on the compartment immediately below the tanks. Once the solution in the chiller is cooled to approximately 4° C., the bottom of the chiller is opened and the chilled solution flows into the electrophoresis tank that is located in the compartment below, whose temperature is maintained by a constant flow of chilled water throughout the remainder of the assay process.

In preferred embodiments, the electrophoresis and post-electrophoresis steps are performed in the absence of an operator's attendance. In exemplary embodiments, the overall time required to perform the cellular assay such as a comet assay can be decreased to about 24 hours, a throughput rate almost twice as high as that of existing technologies.

Figure 4:
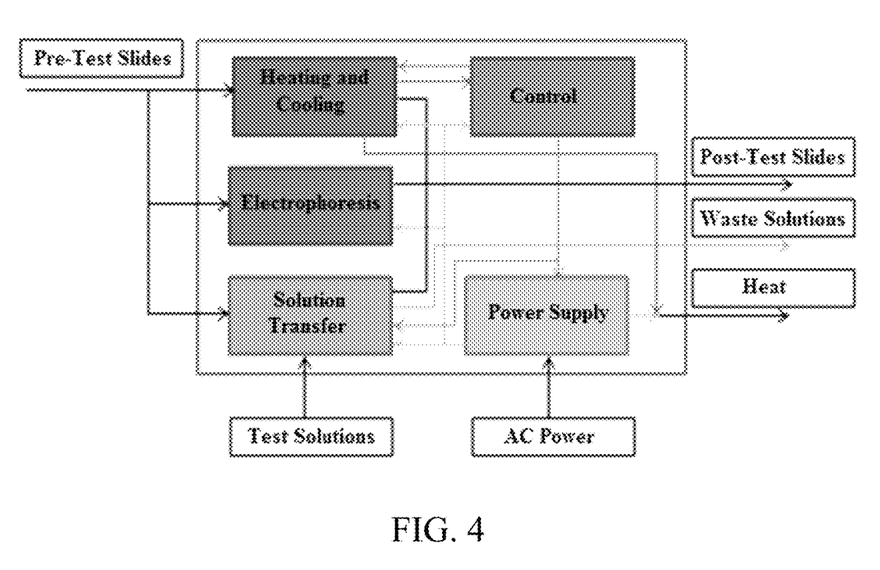
FIG. 4 shows an engineering block diagram outlining the process of the automation of the comet assay apparatus.

In some embodiments, the entire electrophoresis experiment can be automated (FIG. 4). In specific embodiments, the chiller, together with the pump and a switching mechanism, automate the filling, emptying, chilling, and recirculation of all fluids contained in the apparatus. Advantageously, automation enabled by the apparatus provided herein allows an operator to start the assay process and have the option of leaving the apparatus until all steps are completed.

In some embodiments, the chiller equipped with two float sensors and a temperature sensor ensures the chilling and recirculation of solutions such as an electrophoresis buffer through the electrophoresis tank and precisely maintains the solutions at a specific temperature, which is essential for the completion of the assay.

Since the temperature of the apparatus can be controlled between about 4° C. and about 40° C. using various cooling and heating mechanisms provided herein, drying and chilling of the slides required by the assay process advantageously need not to be performed in a refrigerator. In exemplary embodiments, the temperature control system provided herein can maintain ±1° C. of a desired temperature.

Advantageously, the subject invention provides technology for streamlining the entire process of a cellular assay such as a comet assay prior to scoring, allowing for consistent and accurate temperature control as well as preventing possible light contamination due to the handling and transporting of the slides during the assay process.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. S. Shaposhnikov, E. Frengen and A. Collins, 'Increasing the resolution of the comet assay using fluorescent in situ hybridization—a review', Mutagenesis, vol. 24, no. 5, pp. 383-389, 2009.
2. T. Sathya, B. Murthy and N. Vardhini, 'Genotoxicity evaluation of certain Bhasmas using Micronucleus and Comet assays', IJAM, vol. 7, no. 1, 2009.
3. M. Karbaschi, & M. S. Cooke, 'Novel method for the high-throughput processing of slides for the comet assay', Sci. Rep., vol. 4, 7200; DOI:10.1038/srep07200, 2014.
4. COMPAC-50 HTP Comet Assay Tank, 1st ed. Warwickshire, p. 1.

What is claimed is:

1. A method of performing an electrophoresis assay process, comprising:
   providing an apparatus comprising:
   a first compartment, comprising a water tank and at least one additional tank filled with a solution needed for the assay process, each tank being controlled by a solenoid valve;
   a second compartment, comprising a chiller and a first cooling loop that connects together a pump, a liquid cooler, and a thermoelectric device;
   a third compartment, comprising an electrophoresis tank holding at least one removable rack of individual substrates fixated with cellular materials and a second cooling loop that circulates chilled liquid around the electrophoresis tank; and
   a fourth compartment, comprising at least one microcontroller and a power supply, said compartments being connected electrically and controlled by a switch; wherein said method further comprises:
   performing pre-electrophoresis processing steps that comprise lysing the cellular materials and subsequently rinsing the cellular materials;
   performing electrophoresis processing steps by establishing an electrical current across electrodes located at two opposite ends of the electrophoresis tank; and
   performing post-electrophoresis processing steps that comprise one or more of the following: draining fluids in the electrophoresis tank, neutralizing the cellular materials, staining the cellular materials, rinsing the cellular materials, and drying the materials;
   the individual substrates being kept in the electrophoresis tank throughout the assay process, and the temperature as well as the dispensation and circulation of fluids within the apparatus being automated by the microcontroller.

2. The method according to claim 1, wherein the electrophoresis assay process is a single-cell gel electrophoresis assay.

3. The method according to claim 1, wherein the individual substrates are glass slides.

4. The method according to claim 1, wherein the cellular materials comprise a single cell.

5. The method according to claim 1, wherein the pre-electrophoresis, the electrophoresis, and/or the post-electrophoresis processing steps are performed in the absence of an operator.

6. An apparatus for performing a single-cell gel electrophoresis assay process, comprising:
   a first compartment, comprising a water tank and four additional tanks each filled with a solution independently selected from a lysis buffer, a neutralization buffer, an electrophoresis buffer, and a staining solution, each tank being controlled by a solenoid valve;
   a second compartment, comprising a chiller and a first cooling loop that connects together a pump, a liquid cooler, and a Peltier device equipped with both heating and cooling elements;
   a third compartment, comprising an electrophoresis tank holding two or more removable racks of slides each fixated with a single cell, each rack comprising up to 25 slides, and a second cooling loop capable of circulating chilled liquid around the electrophoresis tank, the chiller comprising a temperature sensor and two float sensors; and
   a fourth compartment, comprising at least one microcontroller and a power supply, the four compartments being arranged vertically, the slides being kept in the electrophoresis tank throughout the assay process, and the temperature as well as the dispensation and circulation of fluids within the apparatus being automated by the microcontroller.

7. The apparatus according to claim 6, wherein with respect to the surface of the slides on which the single cells are fixated, the slides are arranged substantially parallel to one other.

\* \* \* \* \*